United States Patent
Boos et al.

[11] Patent Number: 5,679,260
[45] Date of Patent: Oct. 21, 1997

[54] PROCESS FOR SIMULTANEOUSLY REMOVING TUMOUR NECROSIS FACTOR α AND BACTERIAL LIPOPOLYSACCHARIDES FROM AN AQUEOUS LIQUID

[75] Inventors: Karl-Siegfried Boos, Gauting; Dietrich Seidel, Feldafing; Annette Trautwein, Hassloch; Gerold Morsch, Willinghausen, all of Germany

[73] Assignee: B. Braun Melsungen AG, Melsungen, Germany

[21] Appl. No.: 533,742

[22] Filed: Sep. 26, 1995

[30] Foreign Application Priority Data

Oct. 5, 1994 [DE] Germany .................. 44 35 612.9

[51] Int. Cl.$^6$ .................. C07K 1/14; C07K 1/30; C07K 1/34; A61M 1/34
[52] U.S. Cl. .................. 210/723; 210/650; 210/651; 210/660; 210/669; 210/724; 210/725; 210/729; 210/730; 210/749; 210/767; 210/782; 436/177; 436/178; 530/412; 530/414; 530/415; 530/416; 530/417; 530/418; 530/419; 604/4; 604/5
[58] Field of Search .................. 210/650, 651, 210/660, 669, 723, 724, 725, 729, 730, 749, 767, 782; 436/174, 177, 178; 514/54, 56; 604/4, 5, 6; 530/412, 415, 414, 416, 417, 418, 419, 420

[56] References Cited

U.S. PATENT DOCUMENTS

| | | | |
|---|---|---|---|
| 4,648,974 | 3/1987 | Rosskopf et al. | 210/651 |
| 4,908,354 | 3/1990 | Seidel et al. | 514/56 |
| 4,923,439 | 5/1990 | Seidel et al. | 604/6 |
| 4,935,204 | 6/1990 | Seidel et al. | 210/646 |
| 5,403,917 | 4/1995 | Boos et al. | 530/412 |

*Primary Examiner*—John Kim
*Attorney, Agent, or Firm*—Felfe & Lynch

[57] ABSTRACT

Disclosed is a process to remove tumour necrosis factor α (TNFα) or/and bacterial lipopolysaccharides (LPS) from an aqueous liquid, in particular blood, blood plasma or serum, in an extracorporeal perfusion system after removing corpuscular blood components if necessary, wherein (a) the pH value of the body fluid is adjusted to pH<6, (b) a precipitation reagent in the form of a polyanion is added, (c) precipitated substances are removed by filtration or/and centrifugation and (d) the resulting liquid is passed over an anion exchanger.

21 Claims, 1 Drawing Sheet

PROCESS FOR SIMULTANEOUSLY REMOVING TUMOUR NECROSIS FACTOR α AND BACTERIAL LIPOPOLYSACCHARIDES FROM AN AQUEOUS LIQUID

BACKGROUND OF THE INVENTION

The present invention concerns a process for removing tumour necrosis factor α or/and LPS from an aqueous liquid, preferably a body fluid and in particular blood, blood plasma and blood serum in an extracorporeal perfusion system.

The selective elimination of tumour necrosis factor α (TNFα) and/or of bacterial lipopolysaccharides (LPS, synonym: endotoxins) from human blood is desirable from a medical point of view in particular for the treatment of a severe sepsis with impaired organ perfusion, with hypotension or with multi-organ failure ("Intensiv-therapie bei Sepsis und Multiorganversagen", Schuster, H.-P. et., 1993, Springer Verlag, Berlin). The prognosis for septic shock is poor under the present standard therapy. Despite all therapeutic efforts, a lethal outcome must be expected in up to 50% of the patients. The number of deaths caused by septic shock in the USA has been estimated as ca. 100 000 per year (Parillo, J. E., "Septic Shock in Humans" in: Annals of Internal Medicine, Vol. 113, No. 3, 1990, 227–242).

Septic complications arise after humans become infected by gram-negative bacteria. Invasion of the bacteria into the blood stream leads to release of LPS from the outer bacterial cell wall when the bacteria disintegrate. Bacterial lipopolysaccharides have a rod-like form and are composed of three structurally different regions. The carrier of the toxic properties is the lipid A. This subregion with a molecular weight of 2000 daltons is composed of a phosphorylated D-glucosamine-disaccharide to which several long-chained fatty acids are linked in an ester or amide-like manner (Bacterial Endotoxic Lipopolysaccharides, Morrison, D. C., Ryan, J. L. eds., 1992, CRC Press).

The bacterial lipopolysaccharides (LPS) acting as initiating mediators, are the most important toxins in the pathogenesis of septic shock. The clinical picture of sepsis correlates in most cases with the course and the level of the LPS concentration in the blood of the patients (Nitsche, D. et al., Intensive Care Med., 12 Suppl., 1986, 185 ff). The lipopolysaccharides stimulate the phagocytes in the organism denoted macrophages to produce and release TNFα.

TNFα is a hormone of the immune system and belongs to the class of cytokines. The biologically active form of TNFα is composed of an aggregate of three identical polypeptide chains (157 amino acids, molecular weight: $17.4 \times 10^3$ daltons) (Ziegler, E. J., N. Engl. J. Med. 318, 1988, 1533 ff.). Among the cytokines TNFα plays a key role with regard to the pathogenesis of septic shock.

Thus in patients with for example meningococcic sepsis there is a correlation between the TNF concentration in plasma and the severity of septic shock symptoms and the later occurrence of death (Grau, G. E. et al., Immunol. Rev. 112, 1989, 49 ff.). Increased TNF plasma concentrations are also found in patients with parasitic diseases and other infections (Scuderi, P. et al., Lancet II, 1986, 1229 ff.).

From the standpoint of intensive therapy a selective elimination of the pathogenic blood components LPS and TNFα is therefore desirable. This is also particularly the case since for example the administration of highly effective antibiotics (Shenep, J. L., Morgan, K. A., J. Infect. Dis. 150, 1984, 380 ff.), of immunoglobulins (Schedel, F. et al., Crit. Care Med. 19, 1991, 1104 ff.) or of monoclonal antibodies against LPS and TNFα (Werdan, K., Intensivmed. 30, 1993) 201 ff.) were not able to significantly improve the prognosis (survival rate).

Previously porous adsorber materials have been described for the elimination of lipopolysaccharides (endotoxins) from biological liquids such as for example chemically modified polymers (U.S. Pat. No. 3,959,128, U.S. Pat. No. 4,491,660, EP 0 362 876), active charcoal and derivatives (DE 32 30 540 A1), polyethylenimine-coated pearlcellulose (DE-OS 41 14 602A1) and porous support materials with immobilized polymyxin B (U.S. Pat. No. 4,661,260, U.S. Pat. No. 4,576,928). These materials are, however, not suitable for use in an extracorporeal perfusion system since non-pathogenic or protective plasma components are removed in addition to LPS. The materials modified with the cyclic decapeptide polymycin B have on the one hand the desired selectivity but on the other hand their clinical application is very problematic since the ligand is a highly nephrotoxic and neurotoxic substance (Barkow, D. in: "Intensivtherapie bei Sepsis und Multi-organversagen", Schuster, H.-P., ed., 1993, 132 ff., Springer Verlag, Berlin).

Up to now only porous adsorber materials with cation exchanger properties have been described for the isolation and/or elimination of TNFα from biological liquids (Bak, S. J. et al., Korea 9209520, Boos, K.-S. et al., DE 43 31 358 A1).

All previously potentially available possibilities for an extracorporeal sepsis therapy have the major disadvantage that only a single pathogen is eliminated.

In order to favorably influence the clinical course of the clinical picture of sepsis it is, however, desirable from a pathophysiological and therapeutic point of view to simultaneously remove both pathogenic blood components (LPS and TNFα) from the blood circulation of the patient.

This measure initially interrupts the biological mediator cascade and the fatal synergistic effects of the two pathogens TNFα and LPS are effectively abolished.

The object of the present invention is therefore to provide an effective process for extracorporeally removing both factors LPS and TNFα simultaneously from blood, serum or plasma.

THE INVENTION

Figure 1:
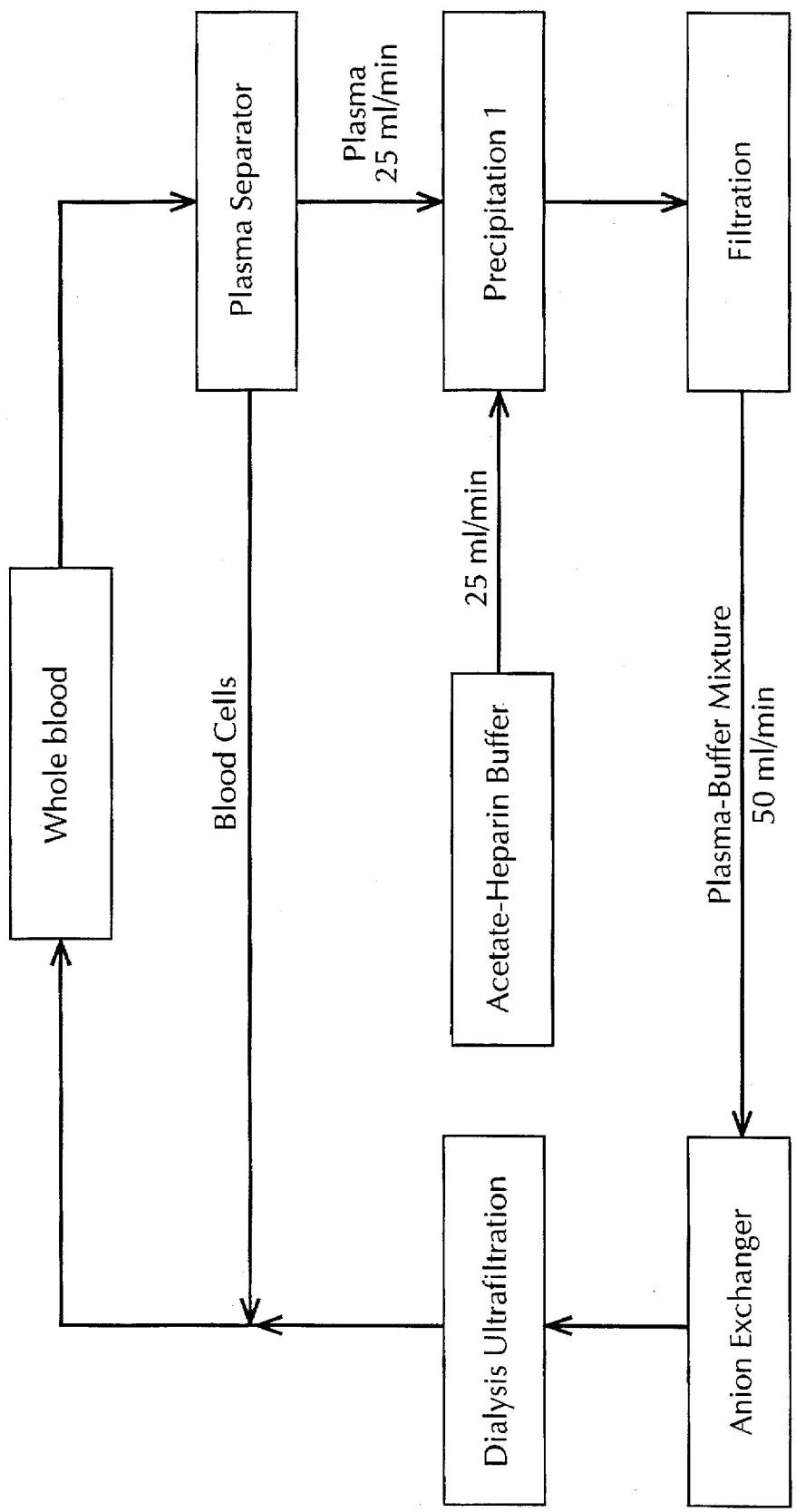
FIG. 1 illustrates the process according to the invention for removing TNF and/or LPS from a body fluid.

This object is achieved by a process for removing tumour necrosis factor α (TNFα) or/and bacterial lipopolysaccharides (LPS) from a body fluid in particular blood, blood serum or serum, in an extracorporeal perfusion system which is characterized in that, after removing corpuscular blood components if necessary, (a) the pH value of the body fluid is adjusted to pH<6, (b) a precipitation reagent in the form of a polyanion is added (c) the precipitated substances are removed by filtration or/and centrifugation and (d) the resulting liquid is passed over an anion exchanger.

The process according to the invention is substantially analogous to the clinical apheresis process described in U.S. Pat. No. 4,908,354, U.S. Pat. No. 4,648,974, EP 0 180 720 and U.S. Pat. No. 4,935,204 (heparin-induced extracorporeal LDL precipitation; HELP), which can be used to selectively remove the blood components low density lipoproteins (LDL) and fibrinogen from the plasma of patients. The disclosure of these references with regard to possibilities of designing the process is therefore incorporated herewith by reference.

The HELP process has previously been used for the chronic treatment of patients with a hereditary disorder of fat metabolism, the severe primary hypercholesterolaemia. These patients have an extremely high risk of dying prematurely as a result of coronary heart disease. Already over 50000 individual treatments with the HELP process have been carried out on about 260 patients (Seidel, D., The HELP Report 1994, MMV "Medizin Verlag, München (1994)).

In the HELP process plasma from the patient which has been filtered over a membrane is firstly admixed in a ratio of 1:1 with a 0.2M acetate-acetic acid buffer (pH 4.85) in the presence of heparin (100 IU/ml). The precipitate of LDL, heparin and fibrinogen produced under these conditions at pH 5.12 is quantitatively separated on a polycarbonate candle filter under recirculating conditions. In a further step the excess precipitating reagent heparin is selectively adsorbed on a DEAE-cellulose anion exchanger and thus removed. The plasma-buffer mixture is subsequently subjected to a bicarbonate dialysis and ultrafiltration in order to adjust the pH value, the volume and the acetate content to physiological conditions. The treated plasma is subsequently mixed with the blood cells and given back to the patient. At present up to 3 liters plasma can be treated with the HELP process. LDL and fibrinogen are quantitatively removed from the treated plasma.

Within the scope of the present invention it was surprisingly found that in the extracorporeal treatment of blood, serum or plasma of patients which exhibited the clinical picture of sepsis up to the point of a septic shock, an efficient simultaneous removal of both pathogenic blood components LPS and TNFα is possible using analogous steps to the HELP process. This enables for the first time a promising clinical sepsis therapy which is urgently required due to the high number of deaths with this clinical picture.

In the process according to the invention a very effective precipitation of TNFα is achieved by addition of an organic or inorganic polyanion and in particular of heparin which is then removed by filtration or centrifugation. In a second step excess polyanion is removed by binding to an anion exchanger which surprisingly also simultaneously and very effectively removes LPS within the scope of the invention. Therefore by using the process according to the invention it is possible to very effectively eliminate both sepsis-causing or accompanying substances from the blood.

Within the scope of the present invention it is preferred that the pH value of the body fluid is adjusted to a value between 4.0 and 5.8 and in particular especially preferably to 5.05 to 5.25. It is expedient to achieve this by adding a buffer, in particular a citrate buffer, a lactate buffer, an acetate buffer or mixtures thereof. The dilution of the plasma by such added buffers is preferably in a ratio of body fluid to buffer solution of 1:5 to 5:1.

The polyanion used according to the invention can be selected from the group of substances comprising heparin, hydrolysed heparin, sulfated glucosaminoglycan or sulfated polysaccharides or mixtures of these substances. Heparin is particularly preferably used as the polyanion.

The polyanion is used in such an amount that the TNFα present in the body fluid is removed as quantitatively as possible. This is preferably an amount of 0.001 to 10 mg/ml body fluid and in the case of heparin and its derivatives in particular an amount of 10 to 400 IU/ml body fluid.

The precipitated substances are then removed by filtration or centrifugation. All filters or flow-through centrifuges suitable for extracorporeal perfusion systems can be used for this. Candle filters are particularly preferred which ensure a particularly efficient separation of the precipitated substances. In this case filter materials are particularly preferably used which have an average pore size of 0.01 to 1.0 µm.

The selective separation of excess polyanion and LPS according to the invention is carried out by means of an anion exchanger.

Within the scope of the invention an anion exchanger is preferably used which has a base support material which is composed of porous glass or/and with silica gel coated with organic polymers or copolymers, cross-linked carbohydrates or/and organic polymers or copolymers.

Furthermore a material is preferably used as the anion exchanger which contains cations or natural, synthetic or semisynthetic polycation chains as functional groups, in which polycation chains can be present in a linear or branched form. Tertiary or/and quarternary amines are particularly preferably used as cation or as polycation chains. Particularly preferred anion exchangers are cross-linked or/and microgranular dialkylaminoalkyl-, dialkylaminoaryl-, trialkylammoniumalkyl- or trialkylammoniumarylcelluloses or/and dialkylaminoalkyl-, dialkylaminoaryl-, trialkylammoniumalkyl- or trialkylammoniumaryl-modified organic polymers or copolymers. In this case DEAE-celluloses and EMD-fractogels are particularly preferred compounds.

After the ultimate removal of the substances TNFα and LPS, the original water content of the liquid is restored by ultrafiltration and/or the physiological pH value is regenerated by an additional dialysis step and/or by addition of a suitable buffer such as bicarbonate buffer in a preferred embodiment of the invention.

When the pH value is adjusted by a buffer solution, the blood or blood plasma is diluted to such an extent that it cannot simply be returned to the patient. A dialysis is therefore preferably carried out and in particular this dialysis is carried out in step (e) against a bicarbonate buffer. The water content of the liquid must also be restored before the blood or the blood plasma can be returned to the patient. It is therefore particularly preferable to carry out an ultrafiltration, but any other method of regenerating the original water content in the body fluid would also appear to be suitable.

In connection with a later return of the plasma purified of TNFα and LPS to the patient, it is obvious to a person skilled in the art that the extracorporeal perfusion system has to be operated under sterile conditions. With regard to the design of the apparatus reference is made in particular to EP 0 180 720.

In summary the process according to the invention enables for the first time the removal of the two main mediators of septic disease states from patient blood in an extracorporeal perfusion system in a simple and effective manner. As a result the fatal cascade is interrupted which, if not treated further, would lead to a lethal outcome for the patients in the majority of cases.

The invention is further illustrated by way of the following examples.

EXAMPLE 1

Elimination of TNFα and of a bacterial lypopolysaccharide from human whole blood using the HELP apheresis process 2100 ml of heparinized (3 IU heparin per ml) human whole blood (haematocrit 44%) freshly collected from healthy donors was admixed with 360 pg/ml of human recombinant TNFα (Serva Company, Heidelberg) and with 3.40 EU/ml (242 pg/ml) of bacterial lipopolysaccharide (*E. coli* 055:B5 endotoxin, BioWhittaker Company, Walkersville, USA).

The whole blood was subjected to a conventional HELP treatment under recirculating conditions (FIG. 1) using the Plasmat-Secura apheresis machine from the Braun Company (Melsungen) and their sterile original disposable material.

In this process the whole blood is pumped at a rate of 70 ml/min over a hollow fibre plasma separator (Haemoselect, 0.2 m² surface, Braun Company, Melsungen) and separated into a blood cell and plasma fraction. The plasma obtained is passed into a mixing chamber at a volume flow of 25 ml/min and admixed at a ratio of 1:1 with 0.2M acetate buffer (pH 4.85) containing heparin (100 IU/ml). The precipitate produced at the resulting pH value of 5.12 is composed, as is well known, of heparin adducts of low density lipoproteins and fibrinogen as well as—according to the invention—of a heparin-TNFα adduct.

The precipitate is removed quantitatively by filtration in a candle filter (polycarbonate precipitate filter, 1.7 m² surface, pore size 0.4 µm, Braun Company, Melsungen). The clarified plasma-buffer mixture subsequently flows through an anion exchanger (DEAE-cellulose, heparin adsorber, Braun Company, Melsungen) at a flow rate of 50 ml/min. This step of the process leads in a known manner to adsorption and elimination of the excess precipitating reagent heparin and, according to the invention, to the simultaneous adsorption and elimination of bacterial lipopolysaccharides (endotoxins).

The plasma-buffer mixture is subsequently subjected to a bicarbonate dialysis and ultrafiltration (1.2 m² surface, Braun Company, Melsungen) at a volume flow of 50 ml/min by which means the physiological pH, electrolyte and volume conditions are restored. The treated plasma is subsequently combined with the blood cell fraction at a volume flow of 25 ml/min and passed into a whole blood bag.

After the recirculating perfusion of 1200 ml plasma which corresponds to one plasma volume in relation to the initial conserved whole blood, a TNFα concentration of 190 pg/ml and a lipopolysaccharide (endotoxin) concentration of 1.36 EU/ml (97 pg/ml) was determined after correcting for dilution via the haematocrit value. The quantitative determination of TNFα was carried out with the enzyme immunoassay TNFα-EAISA from the Medgenix Company, Ratingen. Lipopolysaccharide was quantified using the chromogenic, kinetic Limulus amoebocyte lysate (LAL) test from the Chromogenix AB Company, Mölndal, Sweden.

EXAMPLE 2

Elimination of bacterial lipopolysaccharide and heparin from human plasma under conditions that are analogous to the HELP process with regard to pH and buffer and using a macroporous anion exchanger.

500 ml human plasma (human fresh plasma CPD) was admixed with 11.6 EU/ml (0.82 ng/ml) of bacterial lipopolysaccharide (*E. coli* 055:B5 endotoxin, BioWhittaker Company, Walkersville, USA) and mixed in a ratio of 1:1 with 0.2M acetate buffer (pH 4.85) containing heparin (100 IU/ml) according to the HELP process. The precipitate produced at the resulting pH value of 5.12 of heparin adducts of low density lipoproteins and fibrinogen was centrifuged for 10 min at 3000 g.

The supernatant (960 ml plasma/buffer mixture, pH 5.12) was subsequently pumped at a flow rate of 50 ml/min over a cartridge (filling volume: 380 ml), filled with the anion exchanger Lewatit®OC 1070 (Bayer AG Company, Leverkusen) which had been preconditioned with 2000 ml of a pyrogen-free 0.9% saline solution.

The quantitative determination of lipopolysaccharide and of heparin in the perfused eluate showed that more than 99% of the lipopolysaccharide and over 98% of the heparin had been eliminated from the human plasma by binding to the anion exchanger.

EXAMPLE 3

Adsorption of plasma proteins to a Lewatit® anion exchanger under conditions that are analogous to the HELP process with regard to pH and buffer Analogously to the HELP process 500 ml human plasma (human fresh plasma CPD) was admixed in a ratio of 1:1 with 0.2M acetate buffer (pH 4.85) containing heparin (100 IU/ml). The precipitate produced at the resulting pH value of 5.12 of heparin adducts of low density lipoproteins and of fibrinogen is centrifuged for 10 min at 3000 g.

The supernatant (960 ml plasma/buffer mixture, pH 5.12) was subsequently pumped at a flow rate of 50 ml/min over a cartridge (filling volume: 380 ml), filled with the anion exchanger Lewatit® OC 1070 (Bayer AG Company, Leverkusen) which had been preconditioned with 2000 ml of a pyrogen-free 0.9% saline solution. The plasma/buffer mixture remaining in the dead volume of the cartridge was removed using a 0.1M acetate buffer (pH 5.12, 1000 ml, flow rate: 50 ml/min).

Subsequently the plasma proteins bound to the anion exchanger at pH 5.12 were desorbed under recirculating conditions (30 min) by a 2M saline solution (300 ml) at a flow rate of 30 ml/min while reversing the flow direction.

The quantitative determination of the various plasma proteins listed in Table 1 showed that only 1.77 g of total protein i.e. only 6.1% of the content of the untreated plasma/buffer mixture was adsorptively bound. Of the examined proteins only prealbumin, ceruloplasmin, retinol-binding protein and $\alpha_1$-glycoprotein were eliminated to a significant extent. It is, however, known that these plasma proteins are very rapidly substituted by endogenous synthesis and that a temporary reduction does not cause undesired physiological reactions.

TABLE 1

Adsorption of plasma proteins to a Lewatit ® anion exchanger under conditions that are analogous to the HELP process with regard to pH and buffer

|  | [mg]ᵃ | [%]ᵇ |
|---|---|---|
| Total protein | 1770 | 6.1 |
| Albumin | 1050 | 6.7 |
| Prealbumin | 76 | 53.1 |
| IgA | 22 | 3.1 |
| IgG | 32 | 0.8 |
| IgM | 21 | 3.9 |
| $\beta_2$ microglobulin | 0.002 | 0.8 |
| $\alpha_2$ macroglobulin | 4 | 0.7 |
| Coeruloplasmin | 36 | 33.9 |
| Haptoglobin | 9 | 2.5 |
| Haemopexin | 4 | 1.1 |
| Retinol-binding protein | 10 | 55.5 |
| Ferritin | 0.002 | 1.5 |
| Transferrin | 15 | 1.2 |
| $\alpha_1$-glycoprotein | 190 | 63.3 |
| $\alpha_1$-antitrypsin | 63 | 6.7 |

TABLE 1-continued

Adsorption of plasma proteins to a Lewatit ® anion exchanger under conditions that are analogous to the HELP process with regard to pH and buffer

[mg]$^a$    [%]$^b$ $^a$Adsorbed amount relative to 1000 ml perfusate (human plasma/0.2M acetate buffer, pH 4.85; 1:1)
$^b$Percentage of initial value It will be understood that the specification and examples are illustrative but not limitative of the present invention and that other embodiments within the spirit and scope of the invention will suggest themselves to those skilled in the art.

We claim:

1. A process for the removal of turnout necrosis factor α (TNFα) and/or bacterial lipopolysaccharides (LPS) from a body fluid of at least one of blood, blood plasma or serum containing TNFα and/or LPS in an extracorporeal peffusion system, comprising:
   (a) adjusting the pH value of the body fluid to pH<6;
   (b) adding a polyanion as a precipitation reagent to the body fluid:
   (c) removing precipitated substances containing TNFα and/or LPS by filtration and/or centrifugation to obtain a resulting liquid; and
   (d) passing the resulting liquid over action exchanger.

2. The process of claim 1, wherein corpuscular blood components are removed from the body fluid prior to the pH adjustment.

3. The process of claim 1, wherein the pH value of the fluid is adjusted to 4.0 to 5.8.

4. The process of claim 3, wherein the pH value is adjusted to 5.05 to 5.25.

5. The process of claim 1, wherein the pH value is adjusted by means of a buffer.

6. The process of claim 5, wherein the buffer is a citrate buffer, a lactate buffer, an acetate buffer or mixtures thereof.

7. The process of claim 5, wherein the body fluid is diluted with buffer solution in a ratio of 1:5 to 5:1.

8. The process of claim 1, wherein the polyanion is heparin, hydrolysed heparin, heparin derivatives or fragments, sulfated glycosaminoglycan or sulfated polysaccharides or mixtures thereof.

9. The process of claim 8, wherein the polyanion is heparin.

10. The process of claim 1, wherein the polyanion is used in an amount of 0.001 to 10 mg/ml or 10 to 400 IU/ml in the case of heparin or derivatives thereof relative to the amount of body fluid.

11. The process of claim 1, wherein the precipitated substances are removed by filtration over a filter with an average pore size of 0.01 to 1.0 µm.

12. The process of claim 11, wherein a candle filter is used.

13. The process of claim 1, wherein the precipitated substances are removed by centrifugation with the aid of a flow-through centrifuge.

14. The process of claim 1, wherein the anion exchanger has a base support material made of porous glass and/or silica gel coated with organic polymers or copolymers, cross-linked carbohydrates and/or organic polymers or copolymers.

15. The process of claim 14, wherein the cations or polycations are tertiary and/or quarternary amines.

16. The process of claim 1, wherein the anion exchanger is of a material which contains cations or natural, synthetic or semisynthetic polycation chains as functional groups in which polycation chains are present in a linear or branched form.

17. The process of claim 1, wherein cross-linked and/or microgranular dialkylaminoalkyl-, dialkylaminoaryl-, trialkylammoniumalkyl- or trialkylammoniumaryl-celluloses and/or dialkylaminoalkyl-, dialkylaminoaryl-, trialkyllammoniumalkyl- or trialkylammoniumaryl-modified organic polymers or copolymers are used as the anion exchanger.

18. The process of claim 1, further comprising:
   (e) restoring the original water content of the fluid by ultrafiltration.

19. The process of claim 1, wherein the physiological pH value of the body fluid is rectored by at least one of a dialysis or the addition of a suitable buffer.

20. The process of claim 19, wherein the dialysis is carried out against a bicarbonate buffer.

21. The process of claim 19 wherein the buffer is bicarbonate buffer.

* * * * *